(12) United States Patent
Korth et al.

(10) Patent No.: US 7,423,165 B2
(45) Date of Patent: Sep. 9, 2008

(54) ORGANOSILICON COMPOUNDS

(75) Inventors: Karsten Korth, Grenzach-Wyhlen (DE); Philipp Albert, Lörrach (DE); Reimund Pieter, Bensheim (DE); Oliver Klockmann, Köln (DE); Andre Hasse, Linnich (DE); Ulrich Deschler, Sailauf (DE); Susann Witzsche, Rheinfelden (DE); Inge Kiefer, Schopfheim (DE)

(73) Assignee: Degussa AG, Düsseldorf (DE)

( * ) Notice: Subject to any disclaimer, the term of this patent is extended or adjusted under 35 U.S.C. 154(b) by 485 days.

(21) Appl. No.: 10/872,177

(22) Filed: Jun. 18, 2004

(65) Prior Publication Data

US 2004/0266968 A1    Dec. 30, 2004

(30) Foreign Application Priority Data

Jun. 20, 2003    (DE)    ................. 103 27 624

(51) Int. Cl.
C07F 7/10    (2006.01)
C08G 77/22    (2006.01)

(52) U.S. Cl. ................. 556/427; 528/30; 556/431
(58) Field of Classification Search ................. 556/431
See application file for complete search history.

(56) References Cited

FOREIGN PATENT DOCUMENTS

| DE | 2 255 577 | 6/1974 |
|---|---|---|
| DE | 101 63 941 C1 | 4/2003 |
| EP | 1 285 926 A1 | 2/2003 |
| EP | 1 394 167 A1 | 3/2004 |
| JP | 62-181346 | 8/1987 |

OTHER PUBLICATIONS

Chem. Abstracts 1988:114012: Hirata et al, Abstract of JP62181346, Aug. 8, 1987.*

Voronkov, M.G. et al., Russ. J. Gen. Chem., 1994, pp. 144-145, vol. 64, Nr. 1.2 Beistein Institut zur Foerderung der Chemischen Wissenschaften, Frankfurt-Main, Germany (Database Accession No. BRN 7134835; XP002300368).

* cited by examiner

Primary Examiner—Samuel A Barts
(74) Attorney, Agent, or Firm—Robert G. Weilacher; Smith, Gambrell & Russell

(57) ABSTRACT

Organosilicon compounds of the general formula I

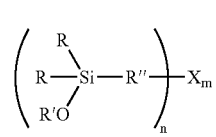

are produced by catalytically reacting silanes of the general formula II

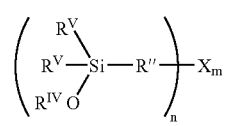

with alcohols of the general formula R'—OH, with the elimination of $R^{IV}OH$, wherein the molar ratio of R—OH to $R^{IV}OH$— groups is at least 1 and $R^{IV}OH$ is removed continuously or discontinuously from the reaction mixture. The organosilicon compounds may be used as coupling agents in filler-reinforced rubber mixtures.

23 Claims, No Drawings

ORGANOSILICON COMPOUNDS

INTRODUCTION AND BACKGROUND

The present invention relates to organosilicon compounds, a process for their production, as well as their use.

Polysulfane-alkyltrialkoxysilanes, such as for example bis[3-triethoxysilylpropyl]tetrasulfane or bis[3-triethoxysilylpropyl]disulfane, and mercaptoalkyltrialkoxy-silanes, such as for example 3-mercaptopropyltrimethoxy-silane or 3-mercaptopropyltriethoxysilane, are used as coupling agents between inorganic materials, for example glass fibres, metals or oxidic fillers, and organic polymers, for example thermosetting materials, thermoplastic materials and elastomers (Angew. Chem. 98, (1986) 237-253).

These coupling agents/bonding agents form stable, chemical bonds with the filler as well as with the polymer and thereby produce a good interaction between the filler surface and the polymer. They reduce the mixture viscosity and facilitate the dispersion of the filler during the mixing procedure.

Furthermore it is known that the use of commercially available silane coupling agents (DE 22 55 577) with three alkoxy substituents on the silicon atom leads to the release of considerable amounts of alcohol during and after the binding to the filler. Since as a rule trimethoxy-substituted and triethoxy-substituted silanes are used, the corresponding alcohols methanol and ethanol are released during the application (Berkemeier, D.; Hader, W.; Rinker, M.; Heiss, G. 'Mixing of silica compounds from the viewpoint of a manufacturer of internal mixers', Gummi, Fasern, Kunststoffe (2001), 54(1), 17-22).

It is also known that methoxy-substituted and ethoxy-substituted silanes are more hydrolysis-active than the corresponding long-chain alkoxy-substituted silanes (E. R. Pohl, F. D. Osterholtz *J. Adhesion Sci. Technology* 6(1) 1992, 127-149) and accordingly can bind more rapidly to the filler, which means that from the economic aspect it has not been possible up to now to dispense with the use of methoxy-substituted and ethoxy-substituted silanes.

Organosilicon compounds of the general formula [RO (R'O)$_2$Si—R"]$_n$X$_m$ and [R'O (RO)$_2$Si—R"]$_n$X$_m$ are known from DE 10163941.

A serious disadvantage in the use of known coupling agents based on alkoxysilanes is the release of stoichiometric amounts of volatile alcohols, such as for example methanol and ethanol, into the environment during and after the binding of the alkoxysilane to the filler.

SUMMARY OF THE INVENTION

An object of the present invention is to provide organosilicon compounds that are not able to release volatile alcohols during the binding to the filler and that at the same time retain the high reactivity with respect to the filler.

The present invention accordingly provides organosilicon compounds of the general formula I

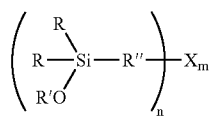

I in which R are identical or different and denote an R'O group or $C_1$-$C_{12}$-alkyl group, preferably a methyl or ethyl group, R' are identical or different and denote a $C_{12}$-$C_{24}$ branched or unbranched single-bond alkyl or alkenyl group, aryl group, aralkyl group or R'''$_3$Si, where R''' denotes a $C_1$-$C_{30}$ branched or unbranched alkyl or alkenyl group, aralkyl group or aryl group, preferably $C_1$-$C_8$, R" is a branched or unbranched, saturated or unsaturated, aliphatic, aromatic or mixed aliphatic/aromatic double-bond $C_1$-$C_{30}$ hydrocarbon group, X denotes SH where n=1 and m=1, SCN where n=1 and m=1, or S where n=2 and m=1-14, and mixtures thereof.

The organosilicon compounds according to the invention of the general formula I may for R preferably contain one or two alkyl groups.

R" for example can be $CH_2$, $CH_2CH_2$, $CH_2CH_2CH_2$, $CH_2CH_2CH_2CH_2$, $CH_2(CH_3)$, $CH_2CH$ $(CH_3)$, $CH(CH_3)$ $CH_2$, $C(CH_3)_2$, $CH_2(C_3H_5)$, $CH_2CH_2CH(CH_3)$, $CH_2CH$ $(CH_3)CH_2$ or

Organosilicon compounds according to the invention of the formula I include

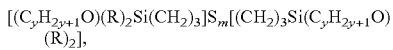

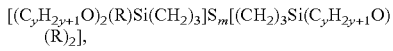

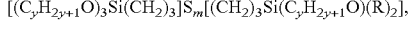

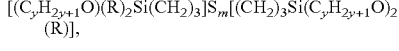

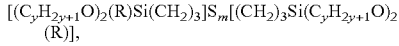

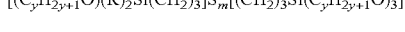

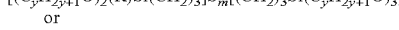

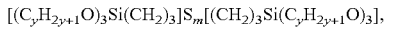

where y is identical or different and denotes a number from 12 to 24, or mixtures of the individual silanes mentioned above.

Organosilicon compounds according to the invention of the formula I include

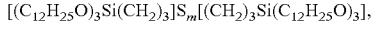

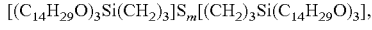

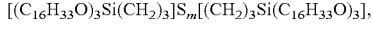

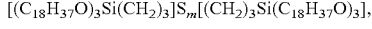

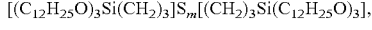

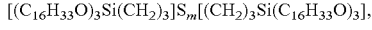

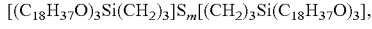

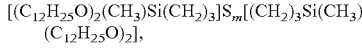

[(C₁₂H₂₅O)(C₁₄H₂₉O)(CH₃)Si(CH₂)₃]S$_m$[(CH₂)₃Si(CH₃)(C₁₂H₂₅O)(C₁₄H₂₉O)],

[(C₁₂H₂₅O)(C₁₄H₂₁O)(CH₃)Si(CH₂)₃]S$_m$[(CH₂)₃Si(CH₃)(C₁₂H₂₅O)(C₁₂H₂₅O)],

[(C₁₂H₂₅O)(C₁₆H₃₃O)(CH₃)Si(CH₂)₃]S$_m$[(CH₂)₃Si(CH₃)(C₁₂H₂₅O)(C₁₆H₃₃O)],

[(C₁₂H₂₅O)(C₁₈H₃₇O)(CH₃)Si(CH₂)₃]S$_m$[(CH₂)₃Si(CH₃)(C₁₂H₂₅O)(C₁₈H₃₇O)],

[(C₁₂H₂₅O)(C₁₈H₃₇O)(CH₃)Si(CH₂)₃]S$_m$[(CH₂)₃Si(CH₃)(C₁₂H₂₅O)(C₁₈H₃₇O)],

[(C₁₄H₂₉O)₂(CH₃)Si(CH₂)₃]S$_m$[(CH₂)₃Si(CH₃)(C₁₄H₂₉O)₂],

[(C₁₄H₂₉O)(C₁₆H₃₃O)(CH₃)Si(CH₂)₃]S$_m$[(CH₂)₃Si(CH₁H₂₉O)(C₁₆H₃₃O)],

[(C₁₄H₂₉O)(C₁₈H₃₇O)(CH₃)Si(CH₂)₃]S$_m$[(CH₂)₃Si(CH₃)(C₁₄H₂₉O)(C₁₈H₃₇O)],

[(C₁₆H₃₃O)₂(CH₃)Si(CH₂)₃]S$_m$[(CH₂)₃Si(CH₃)(C₁₆H₃₃O)₂],

[(C₁₆H₃₃O)(C₁₈H₃₇O)(CH₃)Si(CH₂)₃]S$_m$[(CH₂)₃Si(CH₃)(C₁₆H₃₃O)(C₁₈H₃₇O)],

[(C₁₈H₃₇O)₂(CH₃)Si(CH₂)₃]S$_m$[(CH₂)₃Si(CH₃)(C₁₈H₃₇O)₂],

[(C₁₂H₂₅O)(CH₃)₂Si(CH₂)₃]S$_m$[(CH₂)₃Si(CH₃)₂(C₁₂H₂₅O)],

[(C₁₂H₂₅O)(CH₃)₂Si(CH₂)₃]S$_m$[(CH₂)₃Si(CH₃)₂(C₁₄H₂₉O)],

[(C₁₂H₂₅O)(CH₃)₂Si(CH₂)₃]S$_m$[(CH₂)₃Si(CH₃)₂(C₁₆H₃₃O)],

[(C₁₂H₂₅O)(CH₃)₂Si(CH₂)₃]S$_m$[(CH₂)₃Si(CH₃)₂(C₁₈H₃₇O)],

[(C₁₄H₂₉O)(CH₃)₂Si(CH₂)₃]S$_m$[(CH₂)₃Si(CH₃)₂(C₁₄H₂₉O)],

[(C₁₄H₂₉O)(CH₃)₂Si(CH₂)₃]S$_m$[(CH₂)₃Si(CH₃)₂(C₁₆H₃₃O)],

[(C₁₄H₂₉O)(CH₃)₂Si(CH₂)₃]S$_m$[(CH₂)₃Si(CH₃)₂(C₁₈H₃₇O)],

[(C₁₆H₃₃O)(CH₃)₂Si(CH₂)₃]S$_m$[(CH₂)₃Si(CH₃)₂(C₁₆H₃₃O)],

[(C₁₆H₃₃O)(CH₃)₂Si(CH₂)₃]S$_m$[(CH₂)₃Si(CH₃)₂(C₁₈H₃₇O)],

[(C₁₈H₃₇O)(CH₃)₂Si(CH₂)₃]S$_m$[(CH₂)₃Si(CH₃)₂(C₁₈H₃₇O)], (C₁₂H₂₅O)₃Si—(CH₂)₃—SH, (C₁₂H₂₅O)₂(C₁₄H₂₉O)Si—(CH₂)₃—SH, (C₁₂H₂₅O)₂(C₁₆H₃₃O)Si—(CH₂)₃—SH, (C₁₂H₂₅O)₂(C₁₈H₃₇O)Si—(CH₂)₃—SH, (C₁₂H₂₅O)(C₁₄H₂₉O)(C₁₆H₃₃O)Si—(CH₂)₃—SH, (C₁₂H₂₅O)(C₁₄H₂₉O)(C₁₈H₃₇O)Si—(CH₂)₃—SH, (C₁₂H₂₅O)(C₁₆H₃₃O)(C₁₈H₃₇O)Si—(CH₂)₃—SH, (C₁₄H₂₉O)₃Si—(CH₂)₃—SH, (C₁₄H₂₉O)₂(C₁₂H₂₅O)Si—(CH₂)₃—SH, (C₁₄H₂₉O)₂(C₁₆H₃₃O)Si—(CH₂)₃—SH, (C₁₄H₂₉O)₂(C₁₈H₃₇O)Si—(CH₂)₃—SH, (C₁₄H₂₉O)(C₁₆H₃₃O)(C₁₈H₃₇O)Si—(CH₂)₃—SH, (C₁₆H₃₃O)₃Si—(CH₂)₃—SH, (C₁₆H₃₃O)₂(C₁₂H₂₅O)Si—(CH₂)₃—SH, (C₁₆H₃₃O)₂(C₁₄H₂₉O)Si—(CH₂)₃—SH, (C₁₆H₃₃O)₂(C₁₈H₃₇O)Si—(CH₂)₃—SH, (C₁₈H₃₇O)₃Si—(CH₂)₃—SH, (C₁₈H₃₇O)₂(C₁₂H₂₅O)Si—(CH₂)₃—SH, (C₁₈H₃₇O)₂(C₁₄H₂₉O)Si—(CH₂)₃—SH, (C₁₈H₃₇O)₂(C₁₆H₃₃O)Si—(CH₂)₃—SH, (C₁₂H₂₅O)₂(CH₃)Si—(CH₂)₃—SH, (C₁₂H₂₅O)(C₁₄H₂₉O)(CH₃)Si—(CH₂)₃—SH, (C₁₂H₂₅O)(C₁₆H₃₃O)(CH₃)Si—(CH₂)₃—SH, (C₁₂H₂₅O)(C₁₈H₃₇O)(CH₃)Si—(CH₂)₃—SH, (C₁₄H₂₉O)₂(CH₃)—Si—(CH₂)₃—SH, (C₁₄H₂₉O)(C₁₆H₃₃O)(CH₃)Si—(CH₂)₃—SH, (C₁₄H₂₉O)(C₁₈H₃₇O)(CH₃)Si—(CH₂)₃—SH, (C₁₆H₃₃O)₂(CH₃)—Si—(CH₂)₃—SH, (C₁₆H₃₃O)(C₁₈H₃₇O)(CH₃)Si—(CH₂)₃—SH, (C₁₈H₃₇O)₂(CH₃)—Si—(CH₂)₃—SH, (C₁₂H₂₅O)(CH₃)₂—Si—(CH₂)₃—SH, (C₁₄H₂₉O)(CH₃)₂—Si—(CH₂)₃—SH, (C₁₆H₃₃O)(CH₃)₂—Si—(CH₂)₃—SH, (C₁₈H₃₇O)(CH₃)₂—Si—(CH₂)₃—SH, (C₁₂H₂₅O)₂(C₁₄H₂₉O)Si—(CH₂)₃—SCN, (C₁₂H₂₅O)₂(C₁₆H₃₃O)Si—(CH₂)₃—SCN, (C₁₂H₂₅O)₂(C₁₈H₃₇O)Si—(CH₂)₃—SCN, (C₁₄H₂₉O)₂(C₁₂H₂₅O)Si—(CH₂)₃—SCN, (C₁₄H₂₉O)₂(C₁₆H₃₃O)Si—(CH₂)₃—SCN, (C₁₄H₂₉O)₂(C₁₈H₃₇O)Si—(CH₂)₃—SCN, (C₁₆H₃₃O)₂(C₁₂H₂₅O)Si—(CH₂)₃—SCN, (C₁₆H₃₃O)₂(C₁₄H₂₉O)Si—(CH₂)₃—SCN, (C₁₆H₃₃O)₂(C₁₈H₃₇O)Si—(CH₂)₃—SCN, (C₁₈H₃₇O)₂(C₁₂H₂₅O)Si—(CH₂)₃—SCN, $(C_{18}H_{37}O)_2(C_{14}H_{29}O)Si—(CH_2)_3—SCN$ or $(C_{18}H_{37}O)_2(C_{16}H_{33}O)Si—(CH_2)_3—SCN$.

Condensation products, in other words oligosiloxanes and polysiloxanes, may readily be formed from the silanes according to the invention of the formula I. The oligosiloxanes and polysiloxanes can be obtained by oligomerization or co-oligomerization of the corresponding alkoxysilane compounds of the general formula I by addition of water, and addition of additives and adoption of the preparation procedure known to the person skilled in the art in this field.

These oligomeric or polymeric siloxanes of the compounds of the formula I can be used as coupling reagents for the same applications as the monomeric compounds of the formula I.

The organosilicon compounds according to the invention can also be used as a mixture of organosilicon compounds, for example as mixtures of the organosilicon compounds of the general formula I or as mixtures of the oligomeric or polymeric siloxanes of organosilicon compounds of the general formula I or as mixtures of organosilicon compounds of the general formula I with mixtures of the oligomeric or polymeric siloxanes of organosilicon compounds of the general formula I.

The present invention also provides a process for the production of the organosilicon compounds according to the invention, which is characterized in that silanes of the general formula II

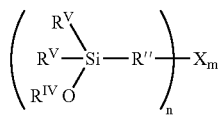

II wherein R" has the meaning given above, $R^V$ are identical or different and denote an $R^{IV}O—$, $C_1$-$C_{12}$-alkyl group, preferably a methyl or ethyl group, $R^{IV}$ are identical or different and denote a methyl or ethyl group, are catalytically reacted with alcohols of the general formula R'—OH in which R' has the meaning given above, with elimination of $R^{IV}OH$, wherein the molar ratio of R'—OH to $R^{IV}O—$ groups is at least 1, preferably at least 1.2, and $R^{IV}OH$ is removed continuously or discontinuously from the reaction mixture.

In the alkoxysilanes that are formed the exact composition of the substance mixtures that are produced with respect to the relative distribution of the alkoxy substituents to one another can be determined by means of high-resolution 29-Si NMR or GPC.

The mixture of homologous alkoxysilane compounds that is formed can be used as such or after separation into individual compounds or isolated fractions.

The alcohols R'OH used for the transesterification may be employed as mixtures of different alcohols or also as pure substances. For example dodecanol, tetradecanol, hexadecanol, octadecanol, 1-eicosanol or natural substances functionalized with hydroxy groups can be used as alcohols R'OH.

The compounds used as catalysts for the transesterification can contain metals or be metal-free.

As metal-free compounds there can be used organic acids such as for example trifluoroacetic acid, trifluoromethanesulfonic acid or p-toluenesulfonic acid, trialkylammonium compounds $R_3NH^+X^-$ or bases, such as for example trialkylamines $NR_3$.

The metal compounds used as catalysts for the transesterification can be transition metal compounds.

As metal compounds for the catalysts there can be used metal chlorides, metal oxides, metal oxychlorides, metal sulfides, metal sulfochlorides, metal alcoholates, metal thiolates, metal oxyalcoholates, metal amides, metal imides or transition metal compounds with multiple bound ligands.

The following can for example be used as metal compounds:

halides, amides or alcoholates of the $3^{rd}$ main group ($M^{3+}$=B,Al,Ga,In,Tl: $M^{3+}(OMe)_3$, $M^{3+}(OEt)_3$, $M^{3+}(OC_3H_7)_3$, $M^{3+}(OC_4H_9)_3$, halides, oxides, sulfides, imides, alcoholates, amides, thiolates and combinations of the aforementioned classes of substituents with multiple bound ligands to compounds of the lanthanide group (rare earths, atomic nos. 58 to 71 in the Periodic System of the Elements), halides, oxides, sulfides, imides, alcoholates, amides, thiolates and combinations of the aforementioned classes of substituents with multiple bound ligands to compounds of the $3^{rd}$ subgroup ($M^{3+}$=Sc,Y,La: $M^{3+}(OMe)_3$, $M^{3+}(OEt)_3$, $M^{3+}(OC_3H_7)_3$, $M^{3+}(OC_4H_9)_3$, $cpM^{3+}(Cl)_2$, cp $cpM^{3+}(OMe)_2$, $cpM^{3+}(OEt)_2$, $cpM^{3+}(NMe_2)$ where cp=cyclopentadienyl), halides, sulfides, amides, thiolates or alcohols of the $4^{th}$ main group ($M^{4+}$=Si,Ge,Sn,Pb: $M^{4+}(OMe)_4$, $M^{4+}(OEt)_4$, $M^{4+}(OC_3H_7)_4$, $M^{4+}(OC_4H_9)_4$; $M^{2+}$=Sn,Pb: $M^{2+}(OMe)_2$, $M^{2+}(OEt)_2$, $M^{2+}(OC_3H_7)_2$, $M^{2+}(OC_4H_9)_2$), tin dilaurate, tin diacetate, $Sn(OBu)_2$, halides, oxides, sulfides, imides, alcoholates, amides, thiolates and combinations of the aforementioned classes of substituents with multiple bound ligands to compounds of the $4^{th}$ subgroup ($M^{4+}$=Ti,Zr,Hf: $M^{4+}(F)_4$, $M^{4+}(Cl)_4$, $M^{4+}(Br)_4$, $M^{4+}(I)_4$, $M^{4+}(OMe)_4$, $M^{4+}(OEt)_4$, $M^{4+}(OC_3H_7)_4$, $M^{4+}(OC_4H_9)_4$, $cp_2Ti(Cl)_2$, $cp_2Zr(Cl)_2$, $cp_2Hf(Cl)_2$, $cp_2Ti(OMe)_2$, $cp_2Zr(OMe)_2$, $cp_2Hf(OMe)_2$, $cpTi(Cl)_3$, $cpZr(Cl)_3$, $cpHf(Cl)_3$, $cpTi(OMe)_3$, $cpZr(OMe)_3$, $cpHf(OMe)_3$, $M^{4+}(NMe_2)_4$, $M^{4+}(NEt_2)_4$, $M^{4+}(NHC_4H_9)_4$), halides, oxides, sulfides, imides, alcoholates, amides, thiolates and combinations of the aforementioned classes of substituents with multiple bound ligands to compounds of the $5^{th}$ subgroup ($M^{5+}$, $M^{4+}$ or $M^{3+}$=V,Nb,Ta: $M^{5+}(OMe)_5$, $M^{5+}(OEt)_5$, $M^{5+}(OC_3H_7)_5$, $M^{5+}(OC_4H_9)_5$; $M^{3+}O(OMe)_3$, $M^{3+}O(OEt)_3$, $M^{3+}O(OC_3H_7)_3$, $M^{3+}(OC_4H_9)_3$; $cpV(OMe)_4$, $cpNb(OMe)_3$, $cpTa(OMe)_3$, $cpV(OMe)_2$, $cpNb(OMe)_3$, $cpTa(OMe)_3$, halides, oxides, sulfides, imides, alcoholates, amides, thiolates and combinations of the aforementioned classes of substituents with multiple bound ligands to compounds of the $6^{th}$ subgroup ($M^{6+}$, $M^{5+}$ or $M^{4+}$=Cr,Mo,W: $M^{6+}(OMe)_6$, $M^{6+}(OEt)_6$, $M^{6+}(OC_3H_7)_6$, $M^{6+}(OC_4H_9)_6$; $M^{6+}O(OMe)_4$, $M^{6+}(OEt)_4$, $M^{6+}O(OC_3H_7)_4$, $M^{6+}O(OC_4H_9)_4$; $M^{6+}O_2(OMe)_2$, $M^{6+}O_2(OEt)_2$, $M^{6+}O_2(OC_4H_9)_2$, $M^{6+}O_2(OSiMe_3)_2$) or halides, oxides, sulfides, imides, alcoholates, amides, thiolates and combinations of the aforementioned classes of substituents with multiple bound ligands to compounds of the $7^{th}$ subgroup ($M^{7+}$, $M^{6+}$, $M^{5+}$ or $M^{4+}$=Mn,Re: $M^{7+}O(OMe)_5$, $M^{7+}(OEt)_5$, $M^{7+}O(OC_3H_7)_5$, $M^{7+}O(OC_4H_9)_5$, $M^{7+}O_2(OMe)_3$, $M^{7+}O_2(OEt)_3$, $M^{7+}O_2(OC_3H_7)_3$, $M^{7+}O_2(OC_4H_9)_3$; $M^{7+}O_2(OSiMe_3)_3$, $M^{7+}O_3(OSiMe_3)$, $M^{7+}O_3(CH_3)$)

The metal compounds and transition metal compounds can have a free co-ordination site on the metal.

As catalysts there can also be used metal compounds or transition metal compounds that are formed by addition of water to hydrolyzable metal compounds or transition metal compounds.

In a particular embodiment titanates, such as for example tetra-n-butyl orthotitanate or tetra-iso-propyl orthotitanate, can be used as catalysts.

The reaction can be carried out at temperatures between 20° and 200° C., preferably between 50° and 150° C., particularly preferably between 70° and 130° C. In order to avoid condensation reactions it may be advantageous to carry out the reaction in an anhydrous environment, ideally in an inert gas atmosphere.

The reaction can be carried out at normal pressure or reduced pressure. The reaction may be carried out continuously or discontinuously.

The organosilicon compounds according to the invention can be used as coupling agents between inorganic materials (for example glass fibres, metals, oxidic fillers, silicas) and organic polymers (for example thermosetting materials, thermoplastic materials, elastomers) or as crosslinking agents and surface modification agents. The organosilicon compounds according to the invention can be used as coupling reagents in filled rubber mixtures, for example tire treads.

The invention also provides rubber mixtures and rubber vulcanizates that are characterized in that they contain rubber, filler, such as for example precipitated silica, optionally further rubber auxiliary substances, as well as at least one of the organosilicon compounds according to the invention.

The organosilicon compounds according to the invention can be used in amounts of 0.1 to 50 wt. %, preferably 0.1 to 25 wt. %, particularly preferably 1 to 20 wt. %, referred to the amount of the rubber that is used.

The addition of the organosilicon compounds according to the invention as well as the addition of the fillers can take place at stock temperatures of 100° to 200° C. The addition may however also take place at lower temperatures of 40° to 100° C., for example together with further rubber auxiliary substances.

The organosilicon compounds according to the invention can be added to the mixing process in pure form as well as supported on an inert organic or inorganic carrier, and can also be reacted beforehand with an organic or inorganic carrier. Preferred carrier materials can be precipitated or pyrogenic silicas, waxes, thermoplastic materials, natural or synthetic silicates, natural or synthetic oxides, special aluminum oxide or carbon blacks.

Furthermore the organosilicon compounds according to the invention can also be reacted beforehand with the filler to be used and then added to the mixing process.

The following substances can be used as fillers for the rubber mixtures according to the invention:

Carbon blacks: the carbon blacks to be used in this connection are produced by the flame black, furnace, gas black or thermal process and have BET surfaces of 20 to 200 m$^2$/g. The carbon blacks may optionally also contain heteroatoms, such as for example Si.

Amorphous silicas, produced for example by precipitation of solutions of silicates or flame hydrolysis of silicon halides with specific surfaces of 5 to 1000 m$^2$/g, preferably 20 to 400 m$^2$/g (BET surface) and with primary particle sizes of 10 to 400 nm. The silicas may optionally also be present as mixed oxides with other metal oxides, such as Al, Mg, Ca, Ba, Zn and titanium oxides.

Synthetic silicates, such as aluminum silicate, alkaline earth metal silicates, such as magnesium silicate or calcium silicate, with BET surfaces of 20 to 400 m$^2$/g and primary particle diameters of 10 to 400 nm.

Synthetic or natural aluminum oxides and hydroxides.

Natural silicates such as kaolin and other naturally occurring silicas.

Glass fibres and glass fibre products (mats, strands) or glass microspheres.

There may preferably be used amorphous silicas, produced by precipitation of solutions of silicates, with BET surfaces of 20 to 400 m$^2$/g, in amounts of 5 to 150 parts by weight, in each case referred to 100 parts of rubber.

The aforementioned fillers can be used alone or in the form of mixtures. In a particularly preferred realization of the process 10 to 150 parts by weight of light-coloured fillers, optionally together with 0 to 100 parts by weight of carbon black, as well as 1 to 20 parts by weight of a compound of the organosilicon compounds according to the invention, in each case referred to 100 parts by weight of rubber, can be used for the production of the mixtures.

Apart from natural rubber, synthetic rubbers are also suitable for the production of the rubber mixtures according to the invention. Preferred synthetic rubbers are described for example in W. Hofmann, Kautschuktechnologie, Genter Verlag, Stuttgart 1980. These comprise inter alia polybutadiene (BR)

polyisoprene (IR)

styrene/butadiene copolymers with styrene contents of 1 to 60 wt. %, preferably 2 to 50 wt. % (SBR)

chloroprene (CR)

isobutylene/isoprene copolymers (IIR)

butadiene/acrylonitrile copolymers with acrylonitrile contents of 5 to 60 wt. %, preferably 10 to 50 wt. % (NBR)

partially hydrogenated or completely hydrogenated NBR rubber (HNBR)

ethylene/propylene/diene copolymers (EPDM)

as well as mixtures of these rubbers. In particular anionically polymerized L-SBR rubbers (solution SBR) with a glass transition temperature above −50° C. as well as their mixtures with diene rubbers are of interest for the production of vehicle tire treads.

The rubber vulcanizates according to the invention may contain further rubber auxiliary substances, such as reaction accelerators, anti-ageing agents, heat ageing inhibitors, light-stability agents, ozone-stability agents, processing auxiliaries, plasticizers, tackifiers, blowing agents, dyes, pigments, waxes, extenders, organic acids, retarding agents, metal oxides as well as activators such as triethanolamine, polyethylene glycol and hexanetriol, which are known to the rubber industry.

The rubber auxiliaries may be used in known amounts, which are governed inter alia by the intended use. Conventional amounts are for example 0.1 to 50 wt. % referred to the rubber. Sulfur or sulfur-donating substances can be used as crosslinking agents. The rubber mixture according to the invention can furthermore contain vulcanization accelerators. Examples of suitable vulcanization accelerators are mercaptobenzothiazoles, sulfenamides, guanidines, thiurams, dithiocarbamates, thioureas and thiocarbonates. The vulcanization accelerators and sulfur are used in amounts of 0.1 to 10 wt. %, preferably 0.1 to 5 wt. % referred to the rubber.

The vulcanization of the rubber mixtures according to the invention may take place at temperatures of 100° to 200° C., preferably 130° to 180° C., optionally under a pressure of 10 to 200 bar. The mixing of the rubbers with the filler, optionally rubber auxiliaries and the organosilicon compound according to the invention may be carried out in known mixing devices such as rollers, internal mixers and mixer-extruders.

The rubber mixtures according to the invention can be used for the production of molded articles, for example for the production of pneumatic tires, tire treads, cable sheathing, hoses, drive belts, conveyor belts, roller coverings, tires, shoes soles, sealing rings and damping elements.

The organosilicon compounds according to the invention have the advantage that no readily volatile alcohol, normally methanol or ethanol, is released and, at the same time, the reactivity with respect to the inorganic filler is furthermore high. The binding of the alkoxysilane to the filler takes place within an economically acceptable time.

In contrast to the volatile, short-chain alcohols of the prior art, the non-volatile, long-chain alcohols are hydrolyzed sufficiently rapidly and split off from the silane skeleton, with the result that a sufficient binding of the organosilicon compounds according to the invention to the filler is ensured during the mixing process. As a result a high reinforcing effect is achieved in the rubber vulcanizates according to the invention, as is shown in the following examples.

DETAILED EMBODIMENT OF THE INVENTION

EXAMPLES

Example 1

119.2 g 3-mercaptopropyl(triethoxy)silane are heated with 288.2 g of a mixture of dodecanol (70 wt. %) and tetradecanol (30 wt. %) and with 0.12 g tetrabutyl orthotitanate at 120° C. for 240 minutes in a 1-liter flask on a rotary evaporator. Ethanol that is thereby produced is distilled off under a vacuum of 50 to 120 mbar within 240 minutes. After cooling, 349.6 g of a colourless, relatively highly viscous liquid are obtained. More than 50 mole % of the ethanol-free compound $(C_{12}H_{25}O/C_{14}H_{29}O)_3Si-C_3H_6-SH$ are formed during the reaction, as can be shown by 1H-NMR and 29Si-NMR. 84% of the ethanol is removed by the reaction from the organoalkoxysilane.

Example 2

119.2 g 3-mercaptopropyl(triethoxy)silane are heated with 288.2 g of a mixture of dodecanol (70 wt. %) and tetradecanol (30 wt. %) and with 0.24 g tetrabutyl orthotitanate at 120° C. for 240 minutes in a 1-liter flask on a rotary evaporator. Ethanol that is thereby produced is distilled off under a vacuum of 50 to 120 mbar within 240 minutes. After cooling, 347.4 g of a colourless, relatively highly viscous liquid are obtained. More than 65 mole % of the ethanol-free compound $(C_{12}H_{25}O/C_{14}H_{29}O)_3Si-C_3H_6-SH$ are formed during the reaction, as can be shown by 1H-NMR and 29Si-NMR. 90% of the ethanol is removed by the reaction from the organoalkoxysilane.

Example 3

178.8 g 3-mercaptopropyl(triethoxy)silane are heated with 435.2 g of a mixture of dodecanol (70 wt. %) and tetradecanol (30 wt. %) and with 0.36 g tetrabutyl orthotitanate at 140° C. for 240 minutes in a 1-liter flask on a rotary evaporator. Ethanol that is thereby produced is distilled off under a vacuum of 120 mbar within 240 minutes. After cooling, 521.6 g of a colourless, relatively highly viscous liquid are obtained. More than 65 mole % of the ethanol-free compound $(C_{12}H_{25}O/C_{14}H_{29}O)_3Si-C_3H_6-SH$ are formed during the reaction, as can be shown by 1H-NMR and 29Si-NMR. 90% of the ethanol is removed by the reaction from the organoalkoxysilane.

Example 4

178.8 g 3-mercaptopropyl(triethoxy)silane are heated with 435.2 g of a mixture of dodecanol (70 wt. %) and tetradecanol (30 wt. %) and with 0.36 g tetrabutyl orthotitanate at 140° C. for 360 minutes in a 1-liter flask on a rotary evaporator. Ethanol that is thereby produced is distilled off under a vacuum of 120 mbar within 360 minutes. After cooling, 522.7 g of a colourless, relatively highly viscous liquid are obtained. More than 65 mole % of the ethanol-free compound $(C_{12}H_{25}O/C_{14}H_{29}O)_3Si-C_3H_6-SH$ are formed during the reaction, as can be shown by 1H-NMR and 29Si-NMR. 90% of the ethanol is removed by the reaction from the organoalkoxysilane.

Example 5

119.2 g 3-mercaptopropyl(triethoxy)silane are heated with 321.6 g tetradecanol and 0.12 g tetrabutyl orthotitanate at 120° C. for 150 minutes in a 1-liter flask on a rotary evaporator. Ethanol that is thereby produced is distilled off under a vacuum of 50 to 120 mbar within 150 minutes. After cooling, 388 g of a colourless, relatively highly viscous liquid are obtained. More than 25 mole % of the ethanol-free compound $(C_{14}H_{29}O)_3Si-C_3H_6-SH$ are formed during the reaction, as can be shown by 1H-NMR and 29Si-NMR. 75% of the ethanol is removed by the reaction from the organoalkoxysilane.

Example 6

119.2 g 3-mercaptopropyl(triethoxy)silane are heated with 321.6 g tetradecanol and 0.24 g tetrabutyl orthotitanate at 120° C. for 150 minutes in a 1-liter flask on a rotary evaporator. Ethanol that is thereby produced is distilled off under a vacuum of 50 to 120 mbar within 150 minutes. After cooling, 388.7 g of a colourless, relatively highly viscous liquid are obtained. More than 25 mole % of the ethanol-free compound $(C_{14}H_{25}O)_3Si-C_3H_6-SH$ are formed during the reaction, as can be shown by 1H-NMR and 29Si-NMR. 75% of the ethanol is removed by the reaction from the organoalkoxysilane.

Example 7

200 g bis[diethoxymethylsilylpropyl]disulfane, $[(EtO)_2(Me)Si-C_3H_6-]_2S_2)$ are heated with 350.3 g dodecanol and 0.4 g tetrabutyl orthotitanate at 115° C. for 120 minutes in a 1-liter flask on a rotary evaporator. Ethanol that is thereby produced is distilled off under a vacuum of 50 to 120 mbar within 120 minutes. After cooling, 455.6 g of a colourless, relatively highly viscous liquid are obtained. More than 80 mole % of the ethanol-free compound $[(C_{12}H_{25}O)_2MeSi-C_3H_6-]_2S_2$ are formed during the reaction, as can be shown by 1H—NMR and 29Si-NMR. 90% of the ethanol is removed by the reaction from the organoalkoxysilane.

Example 8

200 g bis[diethoxymethylsilylpropyl]disulfane, $[(EtO)_2(Me)Si-C_3H_6-]_2S_2)$ are heated with 350.3 g dodecanol and 0.4 g tetrabutyl orthotitanate at 115° C. for 180 minutes in a 1-liter flask on a rotary evaporator. Ethanol that is thereby produced is distilled off under a vacuum of 50 to 120 mbar within 180 minutes. After cooling, 472.2 g of a colourless, relatively highly viscous liquid are obtained. More than 80 mole % of the ethanol-free compound $[(C_{12}H_{25}O)_3MeSi-$ $C_3H_6$—]$_2S_2$ are formed during the reaction, as can be shown by 1H-NMR and 29Si-NMR. 92% of the ethanol is removed by the reaction from the organoalkoxysilane.

Example 9

200 g bis[diethoxymethylsilylpropyl]disulfane, [(EtO)$_2$(Me)Si—$C_3H_6$—]$_2S_2$), are heated with 350.3 g dodecanol and 0.224 g p-toluenesulfonic acid at 115° C. for 120 minutes in a 1-liter flask on a rotary evaporator. Ethanol that is thereby produced is distilled off under a vacuum of 50 to 120 mbar within 120 minutes. After cooling, 471.2 g of a colourless, relatively highly viscous liquid are obtained. More than 80 mole % of the ethanol-free compound [($C_{12}H_{25}$O)$_2$MeSi—$C_3H_6$—]$_2S_2$ are formed during the reaction, as can be shown by 1H-NMR and 29Si-NMR. 92% of the ethanol is removed by the reaction from the organoalkoxysilane.

Example 10

200 g bis[diethoxymethylsilylpropyl]disulfane, [(EtO)$_2$(Me)Si—$C_3H_6$—]$_2S_2$), are heated with 350.3 g dodecanol and 0.224 g p-toluenesulfonic acid at 115° C. for 180 minutes in a 1-liter flask on a rotary evaporator. Ethanol that is thereby produced is distilled off under a vacuum of 50 to 120 mbar within 180 minutes. After cooling, 472.9 g of a colourless, relatively highly viscous liquid are obtained. More than 80 mole % of the ethanol-free compound [($C_{12}H_{25}$O)$_3$MeSi—$C_3H_6$—]$_2S_2$ are formed during the reaction, as can be shown by 1H-NMR and 29Si-NMR. 93% of the ethanol is removed by the reaction from the organoalkoxysilane.

Example 11

159.8 g bis[triethoxysilylpropyl]tetrasulfane (Si 69) are heated with 385.9 g tetradecanol and 0.58 g p-toluenesulfonic acid at 95-100° C. for 240 minutes in a 1-liter flask in a distillation apparatus. Ethanol that is thereby produced is distilled off. After cooling, 471.6 g of a yellow, relatively highly viscous liquid are obtained. More than 65 mole % of the ethanol-free compounds [($C_{14}H_{29}$O)$_3$Si—$C_3H_6$—]$_2S_x$ are formed during the reaction, as can be shown by 1H-NMR and 29Si-NMR. 90% of the ethanol is removed by the reaction from the organoalkoxysilane.

Example 12

159.8 g bis[triethoxysilylpropyl]tetrasulfane (Si 69) are heated with 335.4 g dodecanol and 0.58 g p-toluenesulfonic acid at 110-120° C. for 240 minutes in a 1-liter flask in a distillation apparatus. Ethanol that is thereby produced is distilled off. After cooling, 413.3 g of a yellow, highly viscous liquid are obtained. More than 80 mole % of the ethanol-free compounds [($C_{12}H_{25}$O)$_3$Si—$C_3H_6$—]$_2S_x$ are formed during the reaction, as can be shown by 1H-NMR and 29Si-NMR. 96% of the ethanol is removed by the reaction from the organoalkoxysilane.

Example 13

106.51 g bis[triethoxysilylpropyl]tetrasulfane (Si 69) are heated with 257.3 g tetradecanol and 0.053 g tetrabutyl orthotitanate at 110° C. for 180 minutes in a 1-liter flask in a distillation apparatus. Ethanol that is thereby produced is distilled off. After cooling, 309.8 g of a yellow, relatively highly viscous liquid are obtained. More than 65 mole % of the ethanol-free compounds [($C_{14}H_{29}$O)$_3$Si—$C_3H_6$—]$_2S_x$ are formed during the reaction, as can be shown by 1H-NMR and 29Si-NMR. 90% of the ethanol is removed by the reaction from the organoalkoxysilane.

Example 14

106.51 g bis[triethoxysilylpropyl]tetrasulfane (Si 69) are heated with 257.3 g tetradecanol and 0.053 g tetrabutyl orthotitanate at 130° C. for 180 minutes in a 1-liter flask in a distillation apparatus. Ethanol that is thereby produced is distilled off. After cooling, 306.7 g of a yellow, relatively highly viscous liquid are obtained. More than 80 mole % of the ethanol-free compounds [($C_{14}H_{29}$O)$_3$Si—$C_3H_6$—]$_2S_x$ are formed during the reaction, as can be shown by 1H-NMR and 29Si-NMR. 95% of the ethanol is removed by the reaction from the organoalkoxysilane.

Example 15

118.7 g bis[triethoxysilylpropyl]disulfane (Si 266) are heated with 321.6 g tetradecanol and 0.28 g tetrabutyl orthotitanate at 120° C. for 240 minutes in a 1-liter flask on a rotary evaporator. Ethanol that is thereby produced is distilled off under a vacuum of 50 to 120 mbar within 240 minutes. After cooling, 376.1 g of a colourless, relatively highly viscous liquid are obtained. More than 80 mole % of the ethanol-free compounds [($C_{14}H_{29}$O)$_3$Si—$C_3H_6$—]$_2S_x$ are formed during the reaction, as can be shown by 1H-NMR and 29Si-NMR. 96% of the ethanol is removed by the reaction from the organoalkoxysilane.

Example 16

118.7 g bis[triethoxysilylpropyl]disulfane (Si 266) are heated with 321.6 g tetradecanol and 0.47 g tetrabutyl orthotitanate at 120° C. for 240 minutes in a 1-liter flask on a rotary evaporator. Ethanol that is thereby produced is distilled off under a vacuum of 50 to 120 mbar within 240 minutes. After cooling, 376.0 g of a colourless, relatively highly viscous liquid are obtained. More than 80 mole % of the ethanol-free compounds [($C_{14}H_{29}$O)$_3$Si—$C_3H_6$—]$_2S_x$ are formed during the reaction, as can be shown by 1H-NMR and 29Si-NMR. 96% of the ethanol is removed by the reaction from the organoalkoxysilane.

Example 17

142.5 g bis[triethoxysilylpropyl]disulfane (Si 266) are heated with 335.4 g dodecanol and 0.29 g tetrabutyl orthotitanate at 120° C. for 240 minutes in a 1-liter flask on a rotary evaporator. Ethanol that is thereby produced is distilled off under a vacuum of 50 to 120 mbar within 240 minutes. After cooling, 403.3 g of a colourless, relatively highly viscous liquid are obtained. More than 70 mole % of the ethanol-free compounds [($C_{12}H_{25}$O)$_3$Si—$C_3H_6$—]$_2S_x$ are formed during the reaction, as can be shown by 1H-NMR and 29Si-NMR. 93% of the ethanol is removed by the reaction from the organoalkoxysilane.

Example 18

142.5 g bis[triethoxysilylpropyl]disulfane (Si 266) are heated with 335.4 g dodecanol and 0.58 g tetrabutyl orthotitanate at 120° C. for 240 minutes in a 1-liter flask on a rotary evaporator. Ethanol that is thereby produced is distilled off under a vacuum of 50 to 120 mbar within 240 minutes. After cooling, 403.1 g of a colourless, relatively highly viscous liquid are obtained. More than 75 mole % of the ethanol-free compounds [(C$_{12}$H$_{25}$O)$_3$Si—C$_3$H$_6$—]$_2$S$_x$ are formed during the reaction, as can be shown by 1H-NMR and 29Si-NMR. 94% of the ethanol is removed by the reaction from the organoalkoxysilane.

Example 19

95 g bis[triethoxysilylpropyl]disulfane (Si 266) are heated with 257.3 g tetradecanol and 0.38 g tetrabutyl orthotitanate at 120° C. for 150 minutes in a 1-liter flask on a rotary evaporator. Ethanol that is thereby produced is distilled off under a vacuum of 50 to 120 mbar within 150 minutes. After cooling, 301.6 g of a colourless, relatively highly viscous liquid are obtained. More than 70 mole % of the ethanol-free compounds [(C$_{14}$H$_{29}$O)$_3$Si—C$_3$H$_6$—]$_2$S$_x$ are formed during the reaction, as can be shown by 1H-NMR and 29Si-NMR. 92% of the ethanol is removed by the reaction from the organoalkoxysilane.

Example 20

13.9 g 1-mercaptomethyl(triethoxysilane) are heated with 38.4 g of a mixture of dodecanol (70 wt. %) and tetradecanol (30 wt. %) and 0.1 g tetrabutyl orthotitanate at 100° C. for 240 minutes in a 100 ml flask on a rotary evaporator. Ethanol that is thereby produced is distilled off under a vacuum of 500 to 250 mbar within 240 minutes. After cooling, 44.1 g of a colourless liquid are obtained. More than 50 mole % of the ethanol-free compound (C$_{12}$H$_{25}$O/C$_{14}$H$_{29}$O)$_3$Si—CH$_2$—SH are formed during the reaction, as can be shown by 1H-NMR and 29Si-NMR. 85% of the ethanol is removed by the reaction from the organoalkoxysilane.

Example 21

50 g 1-mercaptomethyl(dimethylethoxysilane) are heated with 61.5 g dodecanol and 0.12 g tetrabutyl orthotitanate at 90° C. for 240 minutes in a 0.5 liter flask on a rotary evaporator. Ethanol that is thereby produced is distilled off under a vacuum of 550 to 250 mbar within 240 minutes. After cooling, 104.5 g of a colourless liquid are obtained. More than 65 mole % of the ethanol-free compound (C$_{12}$H$_{25}$O)Me$_2$Si—CH$_2$—SH are formed during the reaction, as can be shown by 1H-NMR and 29Si-NMR. 70% of the ethanol is removed by the reaction from the organoalkoxysilane.

Example 22

60 g 1-mercaptopropyl(dimethylethoxysilane) are heated with 71.4 g tetradecanol and 0.1 g tetrabutyl orthotitanate at 120° C. for 240 minutes in a 1-liter flask on a rotary evaporator. Ethanol that is thereby produced is distilled off under a vacuum of 150 to 300 mbar within 240 minutes. After cooling, 113.6 g of a colourless liquid are obtained. More than 70 mole % of the ethanol-free compound (C$_{14}$H$_{29}$O)Me$_2$Si—C$_3$H$_6$—SH are formed during the reaction, as can be shown by 1H-NMR and 29Si-NMR. 72% of the ethanol is removed by the reaction from the organoalkoxysilane.

Example 23

Rubber Technology Investigations of the Organosilicon Compounds from Examples 9 and 17

The formulation used for the rubber mixtures is given in the following Table 1. In this, the unit phr denotes proportions by weight, referred to 100 parts of the crude rubber used. The silanes according to the invention are metered in the same molar amounts as the reference compound Si 266, referred to silicon. The general process for the production of rubber mixtures and their vulcanizates is described in the book: "Rubber Technology Handbook", W. Hofmann, Hanser Verlag 1994.

TABLE 1

| Substance | Mixture 1 Reference [phr] | Mixture 2 [phr] | Mixture 3 [phr] |
|---|---|---|---|
| 1$^{st}$ Stage | | | |
| Buna VSL 5025-1 | 96 | 96 | 96 |
| Buna CB 24 | 30 | 30 | 30 |
| Ultrasil 7000 GR | 80 | 80 | 80 |
| Si 266 | 5.8 | — | — |
| Example 9 | — | 11.2 | — |
| Example 17 | — | — | 15 |
| ZnO | 3 | 3 | 3 |
| Stearic acid | 2 | 2 | 2 |
| Naftolen ZD | 10 | 10 | 10 |
| Vulkanox 4020 | 1.5 | 1.5 | 1.5 |
| Protektor G 3108 | 1 | 1 | 1 |
| 2$^{nd}$ Stage | | | |
| Batch Stage 1 | | | |
| 3$^{rd}$ Stage | | | |
| Batch Stage 2 | | | |
| Vulkacit D | 2 | 2 | 2 |
| Vulkacit CZ | 1.5 | 1.5 | 1.5 |
| Perkacit TBzTD | 0.2 | 0.2 | 0.2 |
| Sulfur | 2.1 | 2.1 | 2.1 |

The polymer VSL 5025-1 is an SBR copolymer from Bayer AG polymerized in solution and having a styrene content of 25 wt. %, a vinyl content of 50 wt. %, a cis-1,4 content of 10 wt. % and a trans-1,4 content of 15 wt. %. The copolymer contains 37.5 phr oil and has a Mooney viscosity (ML 1+4/100° C.) of 50±4.

The polymer Buna CB 24 is a cis-1,4-polybutadiene (neodymium type) from Bayer AG with a cis-1,4 content of 97%, a trans-1,4 content of 2%, a 1,2 content of 1% and a Mooney viscosity of 44±5.

Naftolen ZD from Chemetall is used as aromatic oil. Vulcanox 4020 is 6PPD from Bayer AG and Protektor G 3108 is an ozone-stability wax from Paramelt B.V. Vulkacit D (DPG) and Vulkacit CZ (CBS) are commercially available products from Bayer AG, Perkacit TBzTD (tetrabenzylthiuram disulfide) is a product from Flexsys N.V.

The coupling reagent Si 266, a bis-(triethoxysilyl-propyl) disulfide is a product from Degussa AG. Ultrasil 7000 GR is a granulated, readily dispersible precipitated silica from Degussa AG with a BET surface of 170 m$^2$/g.

The rubber mixtures are prepared in an internal mixer according to the mixing protocol given in Table 2.

TABLE 2

| Stage 1 | |
|---|---|
| Settings | |
| Mixing device | Werner & Pfleiderer E-type |
| Rotational speed | 60 min$^{-1}$ |
| Ram pressure | 5.5 bar |
| Empty volume | 1.58 L |
| Degree of filling | 0.58 |
| Throughflow temp. | 70° C. |

TABLE 2-continued

| Mixing procedure | |
|---|---|
| 0 to 1 min | Buna VSL 5025-1 + Buna CB 24 |
| 1 to 3 min | ½ silica, ZnO, stearic acid, Naftolen ZD, silane |
| 3 to 4 min | ½ silica, Vulkanox, Protektor |
| 4 min | Cleaning |
| 4 to 5 min | Mixing |
| 5 min | Aeration |
| 5 to 6 min | Mixing and discharge |
| Batch temp. | 145-155° C. |
| Storage | 24 hours at room temperature |

Stage 2

| Settings | |
|---|---|
| Mixing device | as in Stage 1 up to: |
| Rotational speed | 70 min$^{-1}$ |
| Degree of filling | 0.54 |
| Mixing procedure | |
| 0 to 2 min | Break up Stage 1 batch |
| 2 to 5 min | Maintain batch temperature at 155° C. by varying rotational speed |
| 5 min | Discharge |
| Batch temp. | 155° C. |
| Storage | 4 hours at room temperature |

Stage 3

| Settings | |
|---|---|
| Mixing device | as in Stage 1 up to |
| Rotational speed | 40 min$^{-1}$ |
| Degree of filling | 0.51 |
| Throughflow temp. | 50° C. |
| Mixing procedure | |
| 0 to 2 min | Batch Stage 2, accelerator, sulfur |
| 2 min | discharge and strip on a laboratory mixing mill (diameter 200 mm, length 450 mm, throughflow temperature 50° C.) Homogenization: Cut up 3 × left-hand, 3 × right-hand and withdraw strip material 8 × with narrow roller gap (1 mm) and 3 × with wide roller gap (3.5 mm). |
| Batch temp. | 85-95° C. |

The methods used to test the rubber are summarized in Table 3.

TABLE 3

| Physical Testing | Norm/Conditions |
|---|---|
| ML 1 + 4, 100° C., 3$^{rd}$ Stage | DIN 53523/3, ISO 667 |
| Vulkameter testing, 165° C. t10% (min) | DIN 53529/3, ISO 6502 |
| Tensile test on a ring, 23° C. Tensile strength (MPa) Tensile modulus values (MPa) Elongation at break (%) | DIN 53504, ISO 37 |
| Shore A hardness, 23° C. (SH) | DIN 53 505 |
| Viscoelastic properties, 0 to 60° C., 16 Hz, 50 N initial force and 25 N amplitude force Complex modulus E* (MPa) Loss factor tan δ (—) | DIN 53 513, ISO 2856 |

Table 4 shows the results of the rubber technology tests. The mixtures are vulcanized for 20 minutes at 165° C.

TABLE 4

| | Units | Mixture 1 (Ref.) | Mixture 2 | Mixture 3 |
|---|---|---|---|---|
| Raw Mixture Data | | | | |
| ML 1 + 4 | [—] | 60 | 45 | 42 |
| t10% | [min] | 2.2 | 2.5 | 2.9 |
| Vulcanizate data | | | | |
| Tensile strength | [MPa] | 12.6 | 10.9 | 12.1 |
| Ten. Modulus Value 100% | [MPa] | 2.1 | 1.2 | 1.1 |
| Ten. Modulus Value 300% | [MPa] | 10.4 | 5.8 | 5.6 |
| Ten. Modulus Value 300%/100% | [—] | 5.0 | 4.8 | 5.1 |
| Elongation at break | [%] | 340 | 440 | 490 |
| Shore A hardness | [—] | 64 | 54 | 52 |
| E* (60° C.) | [MPa] | 8.8 | 5.6 | 5.3 |
| E* (0° C.) | [MPa] | 24.2 | 9.2 | 8.4 |
| tan δ (60° C.) | [—] | 0.103 | 0.095 | 0.091 |

As can be seen on the basis of the data in Table 4, the Mooney viscosities of the mixtures 2 and 3 with the silanes according to the invention lie below the level of the reference mixture 1. From this it follows that the mixtures exhibit an easier processability (e.g. on extrusion). Higher t10% values compared to the reference should furthermore be noted. This results in an improved processing reliability since a premature vulcanization is delayed. The reinforcement factor (tensile modulus value 300%/100%) and the tensile strength are at a high value for the mixtures 2, 3 with significantly higher elongations at break compared to the reference mixture 1. Compared to their reference mixture 1, the mixtures with the silanes according to the invention are characterized in particular by a lower dynamic rigidity (E*) at 0° C. Significantly better winter and wet skidding properties should therefore be expected when these mixtures are used as tire treads. In addition these mixtures have a reduced tan δ 60° C. and thus a reduced rolling resistance, resulting in a reduced fuel consumption when the mixtures are used as tire treads.

Thus, a significant improvement in the rubber technology properties compared to the commercially available silanes is found for mixtures containing the silanes according to the invention. This means that, despite the presence of the considerably longer-chain alkoxy groups compared to the conventional methoxy and ethoxy groups, surprisingly there is a very good binding to the silica and to the polymer.

By using these silanes the emission of volatile hydrocarbons is significantly reduced compared to the reference mixture, since instead of ethoxy groups long-chain alkoxy groups with a high boiling point are present as starting groups. The boiling points of the long-chain alcohols formed by hydrolysis of the silane lie above the processing and vulcanization temperatures. Accordingly these remain in the raw mixture and in the vulcanizate and are not discharged into the environment.

Example 24

Rubber Technology Investigations of the Organosilicon Compound from Example 3

The formulation used for the rubber mixtures is given in the following Table 5. In this, the unit phr denotes proportions by weight, referred to 100 parts of the raw rubber used. The silane according to the invention was metered in the same weight as the reference substances Si 69 and Si 266. The sulfur matching that was carried out is necessary inter alia to compensate for the lower sulfur content of the experimental silane. The general procedure for the production of rubber mixtures and their vulcanizates is described in the book: "Rubber Technology Handbook", W. Hofmann, Hanser Verlag 1994.

TABLE 5

| Substance | Mixture 4 Reference [phr] | Mixture 5 Reference [phr] | Mixture 6 [phr] |
|---|---|---|---|
| 1st Stage | | | |
| Buna VSL 5025-1 | 96 | 96 | 96 |
| Buna CB 24 | 30 | 30 | 30 |
| Ultrasil 7000 GR | 80 | 80 | 80 |
| Si 69 | 6.4 | — | — |
| Si 266 | — | 6.4 | — |
| Example 3 | — | — | 6.4 |
| ZnO | 3 | 3 | 3 |
| Stearic acid | 2 | 2 | 2 |
| Naftolen ZD | 10 | 10 | 10 |
| Vulkanox 4020 | 1.5 | 1.5 | 1.5 |
| Protektor G 3108 | 1 | 1 | 1 |
| 2nd Stage | | | |
| Batch Stage 1 | | | |
| 3rd Stage | | | |
| Batch Stage 2 | | | |
| Vulkacit D | 2 | 2 | 2 |
| Vulkacit CZ | 1.5 | 1.5 | 1.5 |
| Perkacit TBzTD | 0.2 | 0.2 | 0.2 |
| Sulfur | 1.5 | 2.1 | 2.2 |

The coupling reagent Si 69, a bis-(triethoxysilyl-propyl)tetrasulfide, and Si 266, a bis-(triethoxysilyl-propyl)disulfide, are products from Degussa AG.

The rubber mixtures are produced in an internal mixer corresponding to the mixing protocol in Table 6.

TABLE 6

| Stage 1 | |
|---|---|
| Settings | |
| Mixing device | Werner & Pfleiderer E-type |
| Rotational speed | 60 min$^{-1}$ |
| Ram pressure | 5.5 bar |
| Empty volume | 1.58 L |
| Degree of filling | 0.56 |
| Throughflow temp. | 70° C. |
| Mixing procedure | |
| 0 to 1 min | Buna VSL 5025-1 + Buna CB 24 |
| 1 to 3 min | ½ silica, ZnO, stearic acid, Naftolen ZD, silane |
| 3 to 4 min | ½ silica, Vulkanox, Protektor |
| 4 min | Cleaning |
| 4 to 5 min | Mixing |
| 5 min | Aeration |
| 5 to 6 min | Mixing and discharge |
| Batch temp. | 145-155° C. |
| Storage | 24 hours at room temperature |
| Stage 2 | |
| Settings | |
| Mixing device | as in Stage 1 up to: |
| Rotational speed | 70 min$^{-1}$ |
| Degree of filling | 0.53 |
| Mixing procedure | |
| 0 to 2 min | Break up Stage 1 batch |
| 2 to 5 min | Maintain batch temperature at 150° C. by varying rotational speed |

TABLE 6-continued

| 5 min | Discharge |
|---|---|
| Batch temp. | 150° C. |
| Storage | 4 hours at room temperature |
| Stage 3 | |
| Settings | |
| Mixing device | as in Stage 1 up to |
| Rotational speed | 40 min$^{-1}$ |
| Degree of filling | 0.50 |
| Throughflow temp. | 50° C. |
| Mixing procedure | |
| 0 to 2 min | Batch Stage 2, accelerator, sulfur |
| 2 min | Discharge and form strip on a laboratory mixing mill (diameter 200 mm, length 450 mm, throughflow temperature 50° C.) Homogenization: Cut up 3 × left-hand, 3 × right-hand and withdraw strip material 8 × with narrow roller gap (1 mm) and 3 × with wide roller gap (3.5 mm). |
| Batch temp. | 85-95° C. |

The methods used for the rubber testing are summarized in Table 7.

TABLE 7

| Physical Testing | Norm/Conditions |
|---|---|
| ML 1 + 4, 100° C., 3rd Stage | DIN 53523/3, ISO 667 |
| Vulkameter testing, 165° C. | DIN 53529/3, ISO 6502 |
| Dmax − Dmin (dNm) | |
| t10% and t90% (min) | |
| Tensile test on a ring, 23° C. | DIN 53504, ISO 37 |
| Tensile strength (MPa) | |
| Tensile modulus values (MPa) | |
| Elongation at break (%) | |
| Shore A hardness, 23° C. (SH) | DIN 53 505 |
| Viscoelastic properties, | DIN 53 513, ISO 2856 |
| 0 to 60° C., 16 Hz, 50 N initial force | |
| and 25 N amplitude force | |
| Complex modulus E* (MPa) | |
| Loss factor tan δ (−) | |
| DIN abrasion, 10 N force (mm$^3$) | DIN 53 516 |
| Ball rebound, 60° C. (%) | ASTM D 5308 |
| Goodrich Flexometer test, | DIN 53533, ASTM D 623 A |
| 0.250 inch stroke, 25 min, 23° C. | |
| Contact temperature (° C.) | |
| Puncture temperature (° C.) | |
| Permanent set (%) | |

Table 8 shows the results of the rubber technology tests. The mixtures are vulcanized for 25 minutes at 165° C.

TABLE 8

| | Units | Mixture 4 (Ref.) | Mixture 5 (Ref.) | Mixture 6 |
|---|---|---|---|---|
| Raw Mixture Data | | | | |
| ML 1 + 4 | [—] | 66 | 63 | 54 |
| Dmax − Dmin | [dNm] | 15.5 | 16.5 | 13.2 |
| t10% | [min] | 1.8 | 2.5 | 1.0 |
| Vulcanizate data | | | | |
| Tensile strength | [MPa] | 14.5 | 13.0 | 14.1 |
| Ten. Modulus Value | [MPa] | 1.8 | 1.9 | 1.7 |

TABLE 8-continued

|  | Units | Mixture 4 (Ref.) | Mixture 5 (Ref.) | Mixture 6 |
|---|---|---|---|---|
| 100% Ten. Modulus Value | [MPa] | 10.5 | 10.4 | 12.2 |
| 300% Ten. Modulus Value | | 5.8 | 5.5 | 7.2 |
| 300%/100% | | | | |
| Elongation at break | [%] | 360 | 350 | 320 |
| Shore A hardness | [—] | 60 | 62 | 55 |
| Ball rebound | [%] | 68.6 | 67.6 | 75.5 |
| Contact temperature | [° C.] | 62 | 61 | 55 |
| Puncture temperature | [° C.] | 101 | 97 | 88 |
| Permanent set | [%] | 2.8 | 2.6 | 2.0 |
| E* (60° C.) | [MPa] | 6.9 | 6.9 | 5.8 |
| E* (0° C.) | [MPa] | 14.8 | 16.8 | 8.9 |
| tan δ (60° C.) | [—] | 0.089 | 0.086 | 0.062 |
| DIN abrasion | [mm$^3$] | 69 | 68 | 47 |

As can be seen from the data in Table 8, the Mooney viscosity of mixture 6 containing the silane according to the invention is significantly lower than the value of the reference mixtures 4 and 5. This results, analogously to Example 23, in a better processability of the raw mixture. As regards the static vulcanizate data, the tensile strengths and elongations at break have comparable values, while the mixture 6 containing the silane according to the invention exhibits a significantly higher reinforcement. This is recognized in the higher tensile modulus value at 300% extension and in the much higher reinforcement factor (tensile modulus value 300%/100%). The very high silica-silane-rubber binding can be seen in this connection.

Compared to the results of the Goodrich Flexometer tests, the mixture 6 containing the silane according to the invention scores better than the reference substances, since it has a lower heat build-up under dynamic stress and a lower permanent deformation. A lower heat build-up is advantageous for a long service life of a dynamically stressed tire tread.

In the same way as in the previous example, the mixture containing the silane according to the invention has a lower dynamic rigidity E* at 0° C. than the reference substances. This denotes a better wet skid behaviour and winter properties. Likewise, the tan δ at 60° C. is also significantly lower compared to the two reference substances, whereby the rolling resistance is also reduced. In addition to these positive properties, the DIN abrasion of the mixture containing the silane according to the invention is also considerably reduced. It is thereby demonstrated that by using the silane according to the invention in a tread mixture, the most important properties of a tire, namely abrasion, wet skidding and rolling resistance are significantly improved.

Overall it is found that when using the silanes according to the invention not only is the emission of volatile hydrocarbons reduced in the processing of the mixtures, but surprisingly the rubber technology properties are also improved.

Example 25

250 g of bis[triethoxysilylpropyl]tetrasulfane (Si 69) are heated with 682.9 g of hexadecanol as well as with 1 g of tetrabutyl orthotitanate at 120° C. for 270 minutes in a 1 liter flask on a rotary evaporator. The silane is added at 100° C. after the alcohol mixture has melted. Ethanol formed in the transesterification is distilled off in vacuo at 20-800 mbar within 270 minutes. After cooling, 801.2 g of a pale yellow, waxy solid are obtained. More than 89 mole % of the ethanol-free compounds [($C_{16}H_{33}O)_3Si$—$C_3H_6$—]$_2S_x$ are formed during the reaction, as can be shown by 1H-NMR and 29Si-NMR. 95% of the ethanol is removed from the product by the reaction.

Example 26

250 g of bis[triethoxysilylpropyl]disulfane (the mean chain length of the polysulfane chains R—$S_x$—R with $S_2$—$S_{10}$ is 2.0; detected by HPLC+NMR) are heated with 766.6 g of hexadecanol as well as with 1 g of tetrabutyl orthotitanate at 120-140° C. in a 1 liter flask on a rotary evaporator. The silane is added at 110° C. after the alcohol mixture has melted. Ethanol formed in the transesterification is distilled off in vacuo at 20-800 mbar within 300 minutes. After cooling, 873.2 g of a waxy solid are obtained. More than 76 mole % of the ethanol-free compound [($C_{16}H_{33}O)_3Si$—$C_3H_6$—]$_2S_2$ is formed during the reaction, as can be shown by 1H-NMR and 29Si-NMR. 94% of the ethanol is removed from the product by the reaction.

Example 27

250 g of bis[triethoxysilylpropyl]disulfane (the mean chain length of the polysulfane chains R—$S_x$—R with $S_2$—$S_{10}$ is 2.0; detected by HPLC+NMR) are heated with a mixture of 79.3 g of tetradecanol (10 wt. %), 357.1 g of hexadecanol (45 wt. %) and 357.1 g of octadecanol (45 wt. %) as well as with 1 g of tetrabutyl orthotitanate at 135° C. in a 1 liter flask on a rotary evaporator. The silane is added at 90° C. after the alcohol mixture has melted. Ethanol formed in the transesterification is distilled off in vacuo at 20-800 mbar within 285 minutes. After cooling, 901.9 g of a waxy solid are obtained. More than 77 mole % of the ethanol-free compounds [($C_{14}H_{29}O/C_{16}H_{33}O/C18H_{37}O)_3Si$—$C_3H_6$—]$_2S_2$ are formed during the reaction, as can be shown by 1H-NMR and 29Si-NMR. The distribution of the alcohols in the silane compounds is random. 94% of the ethanol is removed from bis[triethoxysilylpropyl]disulfane by the reaction.

Example 28

250 g of 3-mercaptopropyl(triethoxy)silane are heated with a mixture 79.5 g of tetradecanol (10 wt. %), 355.7 g of hexadecanol (45 wt. %) and 355.7 g of octadecanol (45 wt. %) as well as with 1 g of tetrabutyl orthotitanate at 130-140° C. in a 1-liter flask on a rotary evaporator. The silane is added at 105° C. after the alcohol mixture has melted. Ethanol formed in the transesterification is distilled off in vacuo at 20-800 mbar within 270 minutes. After cooling, 897.9 g of a colourless, waxy solid are obtained. More than 88 mole % of the ethanol-free compounds [($C_{14}H_{29}O/C_{16}H_{33}O/C_{18}H_{37}O)_3$Si—$C_3H_6$—SH are formed during the reaction, as can be shown by 1H-NMR and 29Si-NMR. The distribution of the alcohols in the silane compounds is random. 96% of the ethanol is removed from 3-mercaptopropyl(triethoxy)silane by the reaction.

Comparison Example 29 (analogous to EP 1394167 A1)

96.6 g of bis[triethoxysilylpropyl]tetrasulfane (Si 69) are heated with 186.6 g of a mixture of hexadecanol and octadecanol (Stenol 1618; Cognis) as well as with 0.05 g of tetrabutyl orthotitanate at 110° C. in a flask on a rotary evaporator. The silane is added at 100° C. after the alcohol mixture has melted. Ethanol formed in the transesterification is distilled off in vacuo at 20-800 mbar within 210 minutes. After cooling, 226.6 g of a yellow, waxy solid are obtained. As can be shown by 1H-NMR and 29Si-NMR, 70% of the EtO—Si groups have been replaced by R—O—Si.

Comparison Example 30 (analogous to EP 1394167 A1)

239.4 g of bis[triethoxysilylpropyl]disulfane (Si 266 from Degussa AG, with a sulfur chain distribution (detectable by HPLC and NMR) $S_x$ where x=2-10, of 2.25) are heated with 385.8 g of a mixture of dodecanol and tetradecanol (Lorol Spezial; Cognis) as well as with 0.12 g of tetrabutyl orthotitanate at 110° C. in a flask on a rotary evaporator. Ethanol formed in the transesterification is distilled off in vacuo at 20-800 mbar within 240 minutes. After cooling, 532.2 g of a pale yellow, highly viscous liquid are obtained. As can be shown by 1H-NMR and 29Si-NMR, 68% of the EtO—Si groups have been replaced by R—O—Si.

Comparison Example 31

2925 g of 3-mercaptopropyl(triethoxy)silane are heated with 4753 g of a mixture of tetradecanol and dodecanol (Lorol Spezial, Cognis) as well as with 1.4 g of tetrabutyl orthotitanate at 110-115° C. in a 10 liter flask in a distillation apparatus. Ethanol formed in the transesterification is distilled off in vacuo at 50-800 mbar. After cooling, 6470 g of a colourless, highly viscous product are obtained. As can be shown for example by 1H-NMR and 29Si-NMR, the distribution of the OR substituents in the silane compounds is purely random. As can be shown by 1H-NMR and 29Si-NMR, 68% of the EtO—Si groups are replaced by R—O—Si.

Example 32

2503.2 g of 3-mercaptopropyl(triethoxy)silane are heated with 6106.6 g of a mixture of tetradecanol and dodecanol (Lorol Spezial, Cognis) as well as with 5 g of tetrabutyl orthotitanate at 105-110° C. for 380 minutes in a 10 liter flask in a distillation apparatus. Ethanol formed in the transesterification is distilled off in vacuo at 15-600 mbar. After cooling, 7183 g of a colourless, highly viscous product are obtained. As can be shown by 1H-NMR and 29Si-NMR, 97% of the EtO—Si groups are replaced by R—O—Si. In the transesterification more than 92 mole % of the ethanol-free compounds [$(C_{12}H_{25}O/C_{14}H_{29}O)_3$Si—$C_3H_6$—SH are formed, as can be shown for example by 1H-NMR and 29Si-NMR. The distribution of the alcohols in the silane compounds is purely random.

Example 33

2002.6 g of 3-mercaptopropyl(triethoxy)silane are mixed with 6108.5 g of hexadecanol as well as with 2 g of tetrabutyl orthotitanate and heated at 95-115° C. for 360 minutes in a 10 liter flask in a distillation apparatus. Ethanol formed in the transesterification is distilled off in vacuo at 15-600 mbar. After cooling, 7022 g of a colourless, solid product are obtained. As can be shown by 1H-NMR and 29Si-NMR, 92% of the EtO—Si groups are replaced by R—O—Si. In the transesterification more than 80 mole % of the ethanol-free compound [$(C_{16}H_{33}O)_3$Si—$C_3H_6$—SH is formed, as can be shown for example by 1H-NMR and 29Si-NMR.

Example 34

Rubber Technology Investigations of the Organosilicon Compounds from Examples 25, 26 and 27

The formulation used for the rubber mixtures is given in the following Table 9. In this, the unit phr denotes proportion by weight, referred to 100 parts of the crude rubber used. The silanes according to the invention are metered in equimolar amounts with respect to 6.4 phr Si 69 referred to silicon. The sulfur metering is adapted so that the free sulfur proportion present in the mixture is the same. The general process for the production of rubber mixtures and their vulcanizates is described in the book: "Rubber Technology Handbook", W. Hofmann, Hanser Verlag 1994.

TABLE 9

| Substance | Mixture 7 Ref. [phr] | Mixture 8 [phr] | Mixture 9 [phr] | Mixture 10 [phr] |
|---|---|---|---|---|
| 1st Stage | | | | |
| Buna VSL 5025-1 | 96 | 96 | 96 | 96 |
| Buna CB 24 | 30 | 30 | 30 | 30 |
| Ultrasil 7000 GR | 80 | 80 | 80 | 80 |
| Si 69 | 6.4 | — | — | — |
| Example 25 | — | 20.6 | — | — |
| Example 26 | — | — | 19.9 | — |
| Example 27 | — | — | — | 20.6 |
| ZnO | 3 | 3 | 3 | 3 |
| Stearic acid | 2 | 2 | 2 | 2 |
| Naftolen ZD | 10 | 10 | 10 | 10 |
| Vulkanox 4020 | 1.5 | 1.5 | 1.5 | 1.5 |
| Protektor G 3108 | 1 | 1 | 1 | 1 |
| 2nd Stage | | | | |
| Batch Stage 1 | | | | |
| 3rd Stage | | | | |
| Batch Stage 2 | | | | |
| Vulkacit D | 2 | 2 | 2 | 2 |
| Vulkacit CZ | 1.5 | 1.5 | 1.5 | 1.5 |
| Perkacit TBzTD | 0.2 | 0.2 | 0.2 | 0.2 |
| Sulfur | 1.5 | 1.5 | 2.1 | 2.1 |

The rubber mixtures are produced in an internal mixer corresponding to the mixing protocol in Table 10.

TABLE 10

| Stage 1 | |
|---|---|
| Settings | |
| Mixing device | Werner & Pfleiderer E-type |
| Rotational speed | 60 min$^{-1}$ |
| Ram pressure | 5.5 bar |
| Empty volume | 1.58 L |
| Degree of filling | 0.55 |
| Throughflow temp. | 70° C. |
| Mixing procedure | |
| 0 to 1 min | Buna VSL 5025-1 + Buna CB 24 |
| 1 to 3 min | ½ silica, ZnO, stearic acid, Naftolen ZD, silane |
| 3 to 4 min | ½ silica, Vulkanox, Protektor |
| 4 min | Cleaning |
| 4 to 5 min | Mixing |
| 5 min | Aeration |
| 5 to 6 min | Mixing and discharge |
| Batch temp. | 145-155° C. |
| Storage | 24 hours at room temperature |

TABLE 10-continued

Stage 2

Settings

| | |
|---|---|
| Mixing device | as in Stage 1 up to: |
| Rotational speed | 70 min$^{-1}$ |
| Degree of filling | 0.53 |

Mixing procedure

| | |
|---|---|
| 0 to 2 min | Break up Stage 1 batch |
| 2 to 5 min | Maintain batch temperature at 150° C. by varying rotational speed |
| 5 min | Discharge |
| Batch temp. | 145-155° C. |
| Storage | 4 hours at room temperature |

Stage 3

Settings

| | |
|---|---|
| Mixing device | as in Stage 1 up to |
| Rotational speed | 40 min$^{-1}$ |
| Degree of filling | 0.51 |
| Throughflow temp. | 50° C. |

Mixing procedure

| | |
|---|---|
| 0 to 2 min | Batch Stage 2, accelerator, sulfur |
| 2 min | Discharge and form strip on a laboratory mixing mill (diameter 200 mm, length 450 mm, throughflow temperature 50° C.) Homogenization: Cut up 3 × left-hand, 3 × right-hand and withdraw strip material 8 × with narrow roller gap (1 mm) and 3 × with wide roller gap (3.5 mm). |
| Batch temp. | <110° C. |

The methods used for the rubber testing are summarized in Table 11.

TABLE 11

| Physical Testing | Norm/Conditions |
|---|---|
| ML 1 + 4, 100° C., 2$^{nd}$ and 3$^{rd}$ Stages | DIN 53523/3, ISO 667 |
| Prevulcanization behaviour, 130° C. | DIN 53523/4, ISO 667 |
| Prevulcanization time t$_5$ | |
| Prevulcanization time t$_{35}$ | |
| Vulkameter testing, 165° C. | DIN 53529/3, ISO 6502 |
| Dmax − Dmin (dNm) | |
| t10% (min) and t90% (min) | |
| Tensile test on a ring, 23° C. | DIN 53504, ISO 37 |
| Tensile strength (MPa) | |
| Tensile modulus values (MPa) | |
| Elongation at break (%) | |
| Shore A hardness, 23° C. (SH) | DIN 53 505 |
| Viscoelastic properties, | DIN 53 513, ISO 2856 |
| 0 to 60° C., 16 Hz, 50 N initial force | |
| and 25 N amplitude force | |
| Complex modulus E* (MPa) | |
| Loss factor tan δ (−) | |
| DIN abrasion, 10 N force (mm$^3$) | DIN 53 516 |
| Ball rebound, 60° C. (%) | ASTM D 5308 |
| Goodrich Flexometer test, | DIN 53533, ASTM D 623 A |
| 0.250 inch stroke, 25 min, 23° C. | |
| Contact temperature (° C.) | |
| Puncture temperature (° C.) | |
| Permanent set (%) | |

Table 12 shows the results of the rubber technology tests. The mixtures are vulcanized for 25 minutes at 165° C.

TABLE 12

| | Units | Mixture 7 (Reference) | Mixture 8 | Mixture 9 | Mixture 10 |
|---|---|---|---|---|---|
| Raw Mixture Data | | | | | |
| ML 1 + 4 2$^{nd}$ Stage | [—] | 79 | 48 | 49 | 48 |
| ML 1 + 4 3$^{rd}$ Stage | [—] | 67 | 41 | 41 | 40 |
| t$_5$ | [min] | 25.7 | 31.6 | 46.0 | 42.0 |
| t$_{35}$ | [min] | 32.3 | 47.1 | 55.6 | 53.4 |
| t10% | [min] | 1.4 | 2.3 | 3.3 | 3.2 |
| Vulcanizate data | | | | | |
| Tensile strength | [MPa] | 16.0 | 14.3 | 13.5 | 13.8 |
| Tensile Modulus Value 100% | [MPa] | 2.0 | 1.1 | 1.1 | 1.1 |
| Tensile Modulus Value 300% | [MPa] | 10.4 | 5.2 | 5.2 | 5.2 |
| Tensile Modulus Value 300%/100% | [—] | 5.2 | 4.7 | 4.7 | 4.7 |
| Elongation at break | [%] | 400 | 570 | 560 | 570 |
| Shore A hardness | [—] | 63 | 52 | 51 | 50 |
| E* (60° C.) | [MPa] | 9.9 | 5.8 | 5.7 | 5.6 |
| E* (0° C.) | [MPa] | 25.7 | 15.3 | 14.9 | 14.7 |
| tan δ (60° C.) | [—] | 0.124 | 0.122 | 0.121 | 0.119 |

As can be seen from the data in Table 12, the advantages of the mixtures 8, 9 and 10 containing the silanes according to the invention lie in the processing behaviour of the mixtures. This is recognized particularly clearly in the significantly lower Mooney viscosities of the mixing stages 2 and 3 compared to the reference compound (mixture 7). The result is an easier processability (for example on extrusion) of the mixtures. In addition to this, the prevulcanization behaviour of the mixtures 8, 9 and 10 is significantly improved, which can be recognized by the higher $t_5$ and $t_{35}$ values compared to the reference compound. Furthermore, significantly higher t10% values compared to the reference compound should be noted. The result is an improved processing reliability since the danger of an otherwise possible premature vulcanization is significantly reduced. The reinforcement factor (tensile modulus value 300%/100%) and the tensile strength for the mixtures 8, 9 and 10 are high, combined with significantly higher elongations at break compared to the reference mixture 7.

The mixtures containing the silanes according to the invention are characterized in particular by a lower dynamic rigidity (E*) at 0° C. compared to their reference mixture 7. These mixtures are therefore expected to have significantly better winter, ice and wet skid properties when used as tire treads. At low temperatures the mixtures harden considerably less than the reference mixture, and accordingly a significantly improved grip on the road can be assumed. In addition these mixtures have a slightly lower tan δ at 60° C. and thus a reduced rolling resistance, resulting in a reduced fuel consumption of the vehicle where they are used as tire treads.

Thus, mixtures containing the silanes according to the invention exhibit a significant improvement in rubber technology properties compared to silanes of the prior art.

By using the silanes according to the invention of the mixtures 8, 9 and 10, the emission of volatile hydrocarbons can be significantly reduced compared to the reference substance. The boiling points of the long-chain alcohols formed by hydrolysis of the silane lie above the processing and vulcanization temperatures. Accordingly these remain in the raw mixture and in the vulcanizate and are not discharged into the environment.

Example 35

Rubber Technology Investigations of the Organosilicon Compound from Example 28

The formulation used for the rubber mixtures is given in the following Table 13. In this, the unit phr denotes proportions by weight, referred to 100 parts of the raw rubber used. The silane according to the invention is metered in the same weight amount as Si 69 and Si 266. The sulfur matching that is carried out is necessary inter alia to compensate for the lower sulfur content of the experimental silane.

TABLE 13

| Substance | Mixture 11 Reference [phr] | Mixture 12 Reference [phr] | Mixture 13 [phr] |
| --- | --- | --- | --- |
| 1st Stage | | | |
| Buna VSL 5025-1 | 96 | 96 | 96 |
| Buna CB 24 | 30 | 30 | 30 |
| Ultrasil 7000 GR | 80 | 80 | 80 |
| Si 69 | 6.4 | — | — |
| Si 266 | — | 6.4 | — |
| Example 28 | — | — | 6.4 |
| ZnO | 3 | 3 | 3 |
| Stearic acid | 2 | 2 | 2 |
| Naftolen ZD | 10 | 10 | 10 |
| Vulkanox 4020 | 1.5 | 1.5 | 1.5 |
| Protektor G 3108 | 1 | 1 | 1 |
| 2nd Stage | | | |
| Batch Stage 1 | | | |
| 3rd Stage | | | |
| Batch Stage 2 | | | |
| Vulkacit D | 2 | 2 | 2 |

TABLE 13-continued

| Substance | Mixture 11 Reference [phr] | Mixture 12 Reference [phr] | Mixture 13 [phr] |
| --- | --- | --- | --- |
| Vulkacit CZ | 1.5 | 1.5 | 1.5 |
| Perkacit TBzTD | 0.2 | 0.2 | 0.2 |
| Sulfur | 1.5 | 2.1 | 2.2 |

The rubber mixtures are produced in an internal mixer corresponding to the mixing protocol in Table 10.

The methods used to test the rubbers are summarised in Table 11.

Table 14 shows the results of the rubber technology tests. The mixtures are vulcanized for 25 minutes at 165° C.

TABLE 14

| | Units | Mixture 11 (Ref.) | Mixture 12 (Ref.) | Mixture 13 |
| --- | --- | --- | --- | --- |
| Raw Mixture Data | | | | |
| ML 1 + 4 | [—] | 67 | 63 | 55 |
| Dmax – Dmin | [dNm] | 17.2 | 17.6 | 17.5 |
| t10% | [min] | 1.4 | 2.5 | 0.9 |
| Vulcanizate data | | | | |
| Tensile strength | [MPa] | 16.0 | 14.2 | 14.5 |
| Ten. Modulus Value 100% | [MPa] | 2.0 | 1.9 | 1.8 |
| Ten. Modulus Value 300% | [MPa] | 10.4 | 9.8 | 10.9 |
| Ten. Modulus Value 300%/100% | [—] | 5.2 | 5.2 | 6.1 |
| Elongation at break | [%] | 400 | 380 | 360 |
| Shore A hardness | [—] | 63 | 63 | 58 |
| Ball rebound | [%] | 64.0 | 61.5 | 70.9 |
| Contact temperature | [° C.] | 67 | 65 | 53 |
| Puncture temperature | [° C.] | 120 | 118 | 99 |
| Permanent set | [%] | 2.9 | 3.1 | 2.2 |
| E* (60° C.) | [MPa] | 9.9 | 9.8 | 7.4 |
| E* (0° C.) | [MPa] | 25.7 | 26.0 | 12.6 |
| tan δ (60° C.) | [—] | 0.124 | 0.123 | 0.095 |
| DIN abrasion | [mm³] | 89 | 94 | 78 |

As can be seen from the data in Table 14, the Mooney viscosity of mixture 13 containing the silane according to the invention is significantly lower than the value of the reference mixtures 11 and 12. This results, analogously to Examples 23, 24 and 34, in a better processability of the raw mixture. As regards the static vulcanizate data, the tensile strengths and elongations at break have comparable values, while the mixture 13 containing the silane according to the invention exhibits a significantly higher reinforcement. This is recognized in the higher tensile modulus value at 300% extension and in the much higher reinforcement factor (tensile modulus value 300%/100%). The very high silica-silane-rubber binding can be seen in this connection. Compared to the results of the Goodrich Flexometer test, there is less thermal build-up under dynamic stress and a lower permanent deformation in the case of mixture 13 compared to the reference substances. The service life of a dynamically stressed tire tread is increased thereby when using the silane of Example 28.

Similarly, as shown in the previous example, the mixture containing the silane according to the invention has a lower dynamic rigidity E* at 0° C. than the reference substances. This means a better wet skid behaviour and ice and winter properties. As in Example 24, the tan δ value at 60° C. is also significantly lower than in the case of the two reference substances, whereby the rolling resistance is also reduced. Tires with a tread containing the silane according to the invention from Example 28 would lead to a significantly lower fuel consumption of a vehicle compared to standard tires containing Si 69. In addition to these positive properties, the DIN abrasion of the mixture containing the silane according to the invention is also considerably reduced. It is thus also shown here, as in Example 24, that by using the silane according to the invention in a tire tread mixture, the most important properties of a tire, namely abrasion, wet skid and rolling resistance are significantly improved.

Example 36

Rubber Technology Investigations of the Organosilicon Compound from Examples 29 and 25

The formulation used for the rubber mixtures is given in the following Table 15. In this, the unit phr denotes proportions by weight, referred to 100 parts of the raw rubber used. The silanes according to the invention are metered in equimolar amounts with respect to 6.4 phr Si 69 referred to silicon.

TABLE 15

| Substance | Mixture 14 Reference [phr] | Mixture 15 [phr] |
| --- | --- | --- |
| 1st Stage | | |
| Buna VSL 5025-1 | 96 | 96 |
| Buna CB 24 | 30 | 30 |
| Ultrasil 7000 GR | 80 | 80 |
| Example 29 | 16.5 | — |
| Example 25 | — | 20.6 |
| ZnO | 3 | 3 |
| Stearic acid | 2 | 2 |
| Naftolen ZD | 10 | 10 |
| Vulkanox 4020 | 1.5 | 1.5 |
| Protektor G 3108 | 1 | 1 |
| 2nd Stage | | |
| Batch Stage 1 | | |
| 3rd Stage | | |
| Batch Stage 2 | | |
| Vulkacit D | 2 | 2 |
| Vulkacit CZ | 1.5 | 1.5 |
| Perkacit TBzTD | 0.2 | 0.2 |
| Sulfur | 1.5 | 1.5 |

The rubber mixtures are prepared in an internal mixer according to the mixing protocol given in Table 10.

The methods used to test the rubber are summarized in Table 11.

Table 16 shows the results of the rubber technology tests. The mixtures are vulcanized for 25 minutes at 165° C.

TABLE 16

| | Units | Mixture 14 (Ref.) | Mixture 15 |
| --- | --- | --- | --- |
| Raw Mixture Data | | | |
| ML 1 + 4 2nd Stage | [—] | 54 | 48 |
| ML 1 + 4 3rd Stage | [—] | 47 | 41 |
| $t_5$ | [min] | 30.9 | 31.6 |
| $t_{35}$ | [min] | 42.7 | 47.1 |
| t10% | [min] | 2.2 | 2.3 |
| Vulcanizate data | | | |
| Tensile strength | [MPa] | 12.9 | 14.3 |
| Ten. Modulus Value 100% | [MPa] | 1.2 | 1.1 |

TABLE 16-continued

| | Units | Mixture 14 (Ref.) | Mixture 15 |
| --- | --- | --- | --- |
| Ten. Modulus Value 300% | [MPa] | 6.0 | 5.2 |
| Ten. Modulus Value 300%/100% | [—] | 5.0 | 4.7 |
| Elongation at break | [%] | 480 | 570 |
| Shore A hardness | [—] | 54 | 52 |

As can be seen on the basis of the data in Table 16, the completely transesterified silane from mixture 15 exhibits a more rapid and higher drop in Mooney viscosity than the silane from mixture 14. In addition the prevulcanization behaviour is better. It is thus evident that the more highly transesterified product according to the invention has at least the same, if not an even higher, binding rate to the silica. This is particularly surprising since it is known that long-chain alkoxy groups are more unreactive as regards hydrolysis than short-chain alkoxy groups, like the almost exclusively used ethoxy group. The opposite property picture would have been expected. The tensile elongation data are of the same order, the silane according to the invention from Example 25 having a significantly higher elongation at break.

Example 37

Rubber Technology Investigations of the Organosilicon Compounds from Examples 30 and 17

The formulation used for the rubber mixtures is given in the following Table 17. In this, the unit phr denotes proportions by weight, referred to 100 parts of the crude rubber used. The silanes according to the invention are metered in equimolar amounts with respect to 6.4 phr Si 69 referred to silicon.

TABLE 17

| Substance | Mixture 16 Reference [phr] | Mixture 17 [phr] |
| --- | --- | --- |
| 1st Stage | | |
| Buna VSL 5025-1 | 96 | 96 |
| Buna CB 24 | 30 | 30 |
| Ultrasil 7000 GR | 80 | 80 |
| Example 30 | 12.8 | — |
| Example 17 | — | 15.0 |
| ZnO | 3 | 3 |
| Stearic acid | 2 | 2 |
| Naftolen ZD | 10 | 10 |
| Vulkanox 4020 | 1.5 | 1.5 |
| Protektor G 3108 | 1 | 1 |
| 2nd Stage | | |
| Batch Stage 1 | | |
| 3rd Stage | | |
| Batch Stage 2 | | |
| Vulkacit D | 2 | 2 |
| Vulkacit CZ | 1.5 | 1.5 |
| Perkacit TBzTD | 0.2 | 0.2 |
| Sulfur | 1.5 | 1.5 |

The rubber mixtures are prepared in an internal mixer according to the mixing protocol given in Table 10.

The methods used to test the rubber are summarized in Table 11.

Table 18 shows the results of the rubber technology tests. The mixtures are vulcanized for 20 minutes at 165° C.

TABLE 18

| Raw Mixture Data | Units | Mixture 16 (Ref.) | Mixture 17 |
|---|---|---|---|
| ML 1 + 4 | [—] | 45 | 42 |
| Dmax – Dmin | [dNm] | 15.4 | 14.0 |
| t10% | [min] | 3.0 | 2.9 |

| Vulcanizate data | Units | Mixture 14 (Ref.) | Mixture 15 |
|---|---|---|---|
| Tensile strength | [MPa] | 12.1 | 12.1 |
| Ten. Modulus Value 100% | [MPa] | 1.3 | 1.1 |
| Ten. Modulus Value 300% | [MPa] | 6.6 | 5.6 |
| Ten. Modulus Value 300%/100% | | 5.1 | 5.1 |
| Elongation at break | [%] | 440 | 490 |
| Shore A hardness | [—] | 54 | 52 |
| Ball rebound | [%] | 66.3 | 67.9 |
| E* (0° C.) | [MPa] | 9.4 | 8.4 |
| tan δ (60° C.) | [—] | 0.091 | 0.091 |

In this example too the silane according to the invention from Example 17 shows, contrary to expectation, advantages in viscosity compared to the less transesterified product from Example 30. In addition there are also advantages in the tensile elongation behaviour on account of the higher elongation at break with the same reinforcement factor. The somewhat higher ball rebound at 60° C. indicates advantages in rolling resistance, while the low E* at 0° C. is advantageous as regards the wet skid behaviour.

Example 38

Rubber Technology Investigations of the Organosilicon Compounds from Examples 31, 32 and 33

The formulation used for the rubber mixtures is given in the following Table 19. In this, the unit phr denotes proportions by weight, referred to 100 parts of the crude rubber used. The silanes according to the invention are metered in equimolar amounts referred to silicon.

TABLE 19

| Substance | Mixture 18 Reference [phr] | Mixture 19 [phr] | Mixture 20 [phr] |
|---|---|---|---|
| 1st Stage | | | |
| Buna VSL 5025-1 | 96 | 96 | 96 |
| Buna CB 24 | 30 | 30 | 30 |
| Ultrasil 7000 GR | 80 | 80 | 80 |
| Example 31 | 5.4 | — | — |
| Example 32 | — | 6.72 | — |
| Example 33 | — | — | 7.92 |
| ZnO | 3 | 3 | 3 |
| Stearic acid | 2 | 2 | 2 |
| Naftolen ZD | 10 | 10 | 10 |
| Vulkanox 4020 | 1.5 | 1.5 | 1.5 |
| Protektor G 3108 | 1 | 1 | 1 |

TABLE 19-continued

| Substance | Mixture 18 Reference [phr] | Mixture 19 [phr] | Mixture 20 [phr] |
|---|---|---|---|
| 2nd Stage | | | |
| Batch Stage 1 | | | |
| 3rd Stage | | | |
| Batch Stage 2 | | | |
| Vulkacit D | 0.25 | 0.25 | 0.25 |
| Vulkacit CZ | 1.5 | 1.5 | 1.5 |
| Perkacit TBzTD | 0.5 | 0.5 | 0.5 |
| Sulfur | 2.2 | 2.2 | 2.2 |

The rubber mixtures are prepared in an internal mixer according to the mixing protocol given in Table 10.

The methods used to test the rubber are summarized in Table 11.

Table 20 shows the results of the rubber technology tests. The mixtures are vulcanized for 25 minutes at 165° C.

TABLE 20

| | Units | Mixture 18 (Ref.) | Mixture 19 | Mixture 20 |
|---|---|---|---|---|
| Raw Mixture Data | | | | |
| ML 1 + 4, 3rd Stage | [—] | 60 | 57 | 57 |
| t5 | [min] | 20.7 | 22.2 | 24.1 |
| t35 | [min] | 24.5 | 28.1 | 32.0 |
| t10% | [min] | 2.0 | 2.1 | 2.3 |
| Vulcanizate data | | | | |
| Tensile strength | [MPa] | 12.2 | 12.6 | 12.0 |
| Ten. Modulus Value 100% | [MPa] | 1.7 | 1.8 | 1.8 |
| Ten. Modulus Value 300% | [MPa] | 11.3 | 11.5 | 11.9 |
| Ten. Mod. Value 300%/100% | [—] | 6.6 | 6.4 | 6.6 |
| Elongation at break | [%] | 310 | 320 | 300 |
| Shore A hardness | [—] | 56 | 58 | 56 |
| E* (0° C.) | [MPa] | 12.3 | 10.4 | 9.8 |
| tan δ (60° C.) | [—] | 0.102 | 0.096 | 0.095 |
| Ball rebound, 60° C. | [%] | 71.2 | 72.2 | 72.3 |

In this example too the silanes according to the invention from Examples 32 and 33 exhibit the similarly already described advantages as regards viscosity and processing behaviour compared to the less transesterified product from Example 31. The prevulcanization behaviour is also improved. This leads to a higher processing reliability, for example on extrusion. It has to be realized that the chain length of the long-chain alkoxy groups has significantly less influence on the overall rubber technology values than does the degree of transesterification. This is recognized by the fact that the differences in the rubber values of the mixtures 19 and 20 are less compared to the reference mixture 18.

Further modifications and variations of the foregoing will be apparent to those skilled in the art and are intended to be encompassed by the claims appended hereto.

German priority application 103 27 624.6 of Jun. 20, 2003 is relied on and incorporated herein by reference.

We claim:
1. An organosilicon compounds of the formula I

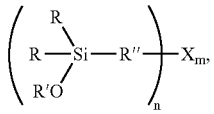
I in which R are identical or different and denote an R'O group or $C_1$-$C_{12}$-alkyl group, R' are identical or different and denote a $C_{12}$-$C_{24}$ branched or unbranched single-bond alkyl or alkenyl group, aryl group, aralkyl group or R'''$_3$Si, where R''' denotes a $C_1$-$C_{30}$ branched or unbranched alkyl or alkenyl group, aralkyl group or aryl group, R'' is a branched or unbranched, saturated or unsaturated, aliphatic, aromatic or mixed aliphatic/aromatic double-bond $C_1$-$C_{30}$ hydrocarbon group, X denotes SH where n=1 and m=1, SCN where n=1 and m=1, or S where n=2 and m=1-14, and mixtures thereof.

2. The organosilicon compound according to claim 1, wherein R is methyl or ethyl.

3. The organosilicon compound according to claim 1, wherein R''' is $C_1$-$C_8$ alkyl or alkenyl.

4. The organosilicon compound according to claim 1, wherein R is one or two alkyl groups.

5. The organosilicon compound according to claim 1, wherein R'' is $CH_2$, $CH_2CH_2$, $CH_2CH_2CH_2$, $CH_2CH_2CH_2CH_2$, $CH_2(CH_3)$ $CH_2CH(CH_3)$, $CH_2CH(CH_3)$, $CH(CH_3)CH_2$, $C(CH_3)_2$, $CH_2(C_3H_5)$, $CH_2CH_2CH(CH_3)$, $CH_2CH(CH_3)CH_2$ or

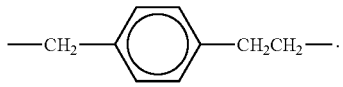

6. An inert organic or inorganic carrier supporting thereon the organosilicon compound according to claim 1.

7. An oligomer or polymer made from an organosilicon compound according to claim 1.

8. A process for the production of the organosilicon compound according to claim 1, comprising catalytically reacting a silane of the formula II

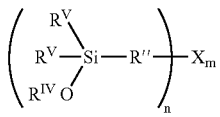
II wherein $R^V$ are identical or different and denote an $R^{IV}$ O—, or $C_1$-$C_{12}$-alkyl group, $R^{IV}$ are identical or different and denote a methyl or ethyl group, with an alcohol of the formula R'—OH eliminating $R^{IV}$ OH, wherein the molar ratio of R'—OH to $R^{IV}$ O— groups is at least 1 and $R^{IV}$ OH is removed continuously or discontinuously from the reaction mixture.

9. The process according to claim 8, wherein a pure alcohol or alcohol mixture is used as the alcohol of the formula R'—OH.

10. Process according to claim 8, wherein a metal-free or metal-containing catalyst is used as catalyst.

11. Process according to claim 10, wherein a compound of the $3^{rd}$-$7^{th}$ group, of the $13^{th}$-$14^{th}$ group and/or of the lanthanide group is used as metal.

12. Process according to claim 11, wherein a titanium alkoxide is used as metal containing catalyst.

13. Process according to claim 8, wherein an organic acid is used as catalyst.

14. Process according to claim 8, wherein the reacting is carried out under the exclusion of moisture and oxygen and under reduced pressure.

15. A vulcanizible rubber mixture, comprising rubber, filler, optionally further rubber auxiliary substances, as well as at least one organosilicon compound according to claim 1.

16. A vulcanized rubber mixture comprising rubber, a filler and at least one organosilicon compound according to claim 1.

17. A moulded article made from the rubber mixtures according to claim 16.

18. An article formed from the vulcanizible rubber mixture of claim 15 in the form of a pneumatic tire, tire tread, cable sheathing, hose, drive belt, conveyor belt, roller covering, tire, shoe sole, sealing ring or damping element.

19. The organosilicon compound according to claim 1 which is:

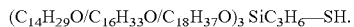

20. The inert organic or inorganic carrier according to claim 6, wherein the organosilicon compound is:

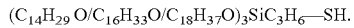

21. The oligomer or polymer according to claim 7 wherein the organosilicon compound is:

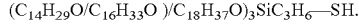

22. The vulcanizable rubber mixture according to claim 15 wherein the organosilicon compound is:

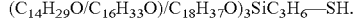

23. The vulcanized rubber mixture according to claim 16 wherein the organosilicon compound is:

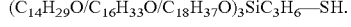

* * * * *